(12) United States Patent
Toth

(10) Patent No.: US 6,359,957 B1
(45) Date of Patent: Mar. 19, 2002

(54) FET SWITCHING METHOD AND APPARATUS FOR MULTI-SLICE CT DETECTOR

(75) Inventor: Thomas L. Toth, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/745,319

(22) Filed: Dec. 21, 2000

(51) Int. Cl.[7] .................................................. A61B 6/03

(52) U.S. Cl. ............................................ 378/19; 378/15

(58) Field of Search ................................ 378/4, 15, 19, 378/901

(56) References Cited

U.S. PATENT DOCUMENTS 6,047,040 A * 4/2000 Hu et al. ........................ 378/19
6,188,745 B1 * 2/2001 Gordon ......................... 379/19

* cited by examiner

Primary Examiner—David V. Bruce
(74) Attorney, Agent, or Firm—Quarles & Brady, LLP; Christian G. Cabou

(57) ABSTRACT

A method and processor for running a pulse sequencing program to perform the method for use with a multi-slice CT system wherein the system includes detector elements arranged in rows for collecting data corresponding to separate slices of an object to be imaged, the system also including fewer acquisition channels than detector elements wherein the method includes alternately connected each acquisition channel to at least first and second elements to acquire data corresponding to each element that can subsequently be combined to form a separate image for each element row in the array.

18 Claims, 3 Drawing Sheets

FET SWITCHING METHOD AND APPARATUS FOR MULTI-SLICE CT DETECTOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates generally to computed tomography (CT) imaging and, more particularly, to methods and apparatus for collecting data corresponding to every element in a CT array to generate a large number of separate slice images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurement, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

During data acquisition the table is translated through the gantry during gantry rotation such that a "helical" data set is collected. An exemplary helical acquisition system is described in U.S. Pat. No. 5,974,110. As well known in the art table translation speed is related to the number of rows of data that can be collected during helical acquisition. To this end, table translation speed can be increased by increasing the number of rows of data collected.

A typical detector array includes a plurality of detector modules, each module forming a flat detector surface. The modules are positioned together so as to form an arc that is essentially centered on the X-ray source. Under each module surface a typical module includes rows and columns of detector elements aligned with X and Z coordinates, respectively. Detector elements are relatively small (e.g., 1.25 mm across). The modules are typically arranged side-by-side to form an array arc with module rows aligned so that data corresponding to a single array row can be used to generate a single thin slice image through a patient.

In addition to including the above described hardware a typical CT system also includes acquisition circuitry that acquires the intensity signals generated by the detector elements, converts the intensity signals into the CT counts and stores the CT counts as data for subsequent image reconstruction via back projection or the like.

There are many different CT applications and each application may ideally require data corresponding to either thin or thick image slices depending upon the application. For this reason many CT systems include switches that allow a user to cause acquisition channels to effectively sum the data from several adjacent array rows during acquisition. Thus, for example, to collect data for a patient slice that is twice as wide as the data corresponding to a single array row, the acquisition channels can be linked to the rows to collect projection data for two adjacent rows simultaneously. Similarly the acquisition channels can be linked to collect data from four adjacent rows simultaneously to generate an even thicker slice image. For exemplary prior art that teaches systems of this type see U.S. Pat. Nos. 5,291,402 and 5,982,846.

Recognizing the need to generate both thick and thin slice images to decrease detector module connector density and, in an attempt to minimize overall system costs, many CT system designers have opted to provide systems with fewer acquisition channels than detector elements. For example, an exemplary module may include 16 rows and 16 columns of elements for a total of 256 elements and the system may only include 128 acquisition channels to acquire the signals from the 256 elements (i.e., a 2 to 1 ratio of elements to acquisition channels). In this case, during data acquisition several different acquisition options are selectable including data corresponding to 1 through 8 separate thin slice images and data corresponding to 2 row thick slice images, 3 row thick slice images and 4 row thick slice images.

While more than 8 thin slice images are not routinely required in CT applications and therefore are not generally supported by CT hardware, there are certain applications where additional thin slice images are required. For instance, in the case of cardiac and CT angiography (CTA) procedures large numbers of thin slice images must be acquired quickly to facilitate efficient clinical practice. In these cases collection of 16 thin slice images instead of 8 is useful.

In addition, as indicated above, during helical data acquisition it is advantageous to collect data corresponding to as many rows as possible so that table translation speed can be maximized.

One solution to increase the number of rows of data collected is to use the system described above twice to collect data corresponding to 8 thin slice images each use for a total of 16 images. Unfortunately, not only does this option require additional time but it also may lead to collecting data corresponding to differing patient positions (i.e., a patient may move or breath, etc., between acquisitions).

Another solution is to provide additional acquisition circuitry so that there is a separate channel for every detector element in an array. This option, while possible, would increase overall system cost appreciably and therefore is not optimal.

BRIEF SUMMARY OF THE INVENTION

An exemplary embodiment of the invention is to be used with a CT imaging system including less acquisition channels than detector elements such that separate data-sets for each element cannot be acquired simultaneously via the acquisition channels, the method for acquiring data corresponding to a number of elements that is greater than the number of acquisition channels during an acquisition period and comprising the steps of: for at least one acquisition channel, (a) during a first sub-period: acquiring a first data-set corresponding to a first detector element and storing the first data-set(b)during a second sub-period: acquiring a second data-set corresponding to a second detector element and storing the second data-set.

The above describe method enables collection of data corresponding to more elements than there are acquisition channels so that the acquired data can be used to construct many images corresponding to thin slices through an object being imaged. More specifically, where the elements are arranged in rows and columns to form an array and the array is mounted to a gantry for rotation about a rotation axis parallel to the columns so that data can be collected corresponding to several gantry positions, the method enables acquisition of data that can be used to generate a separate image for each one of the array rows or, in the case of helical imaging, to simultaneously collect data corresponding to a relatively greater number of rows so that table translation speed can be maximized.

In the description, reference is made to the accompanying drawings which form a part hereof, and in which there is shown a preferred embodiment of the invention. Such embodiment does not necessarily represent the full scope of the invention and reference is made therefor, to claims herein for interpreting the scope of the invention.

DETAILED DESCRIPTION OF THE INVENTION

Figure 1:
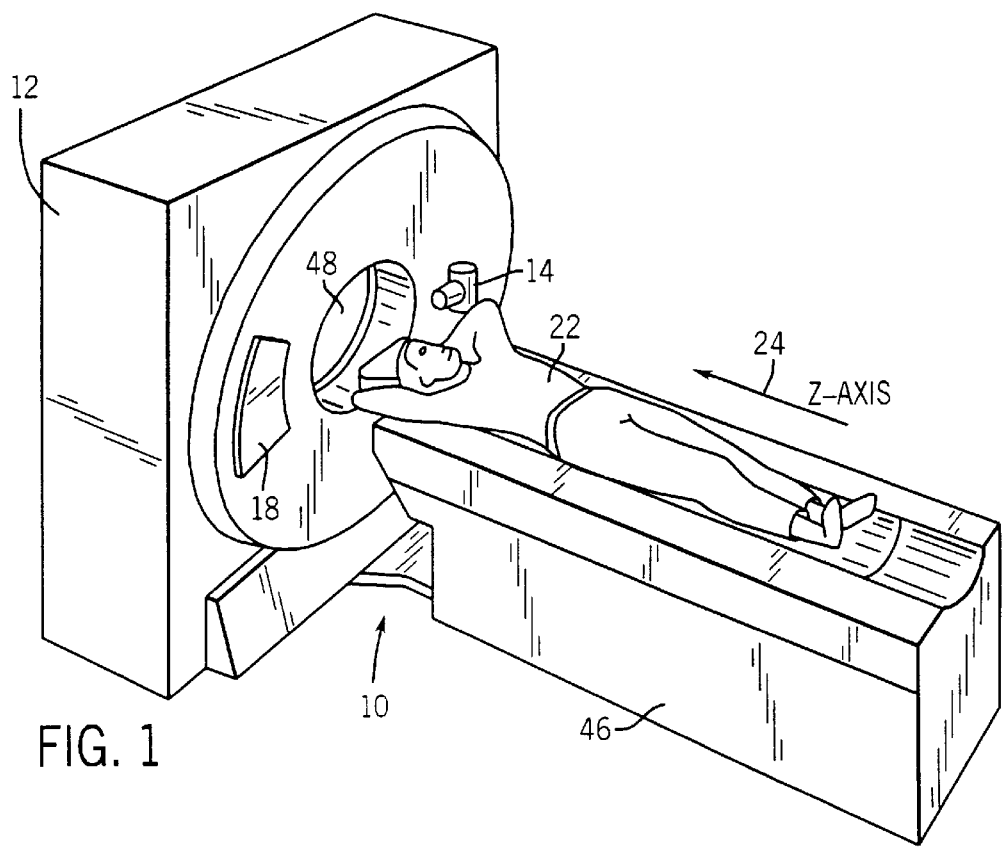
FIG. 1 is a is a perspective view of a CT imaging system
Figure 2:
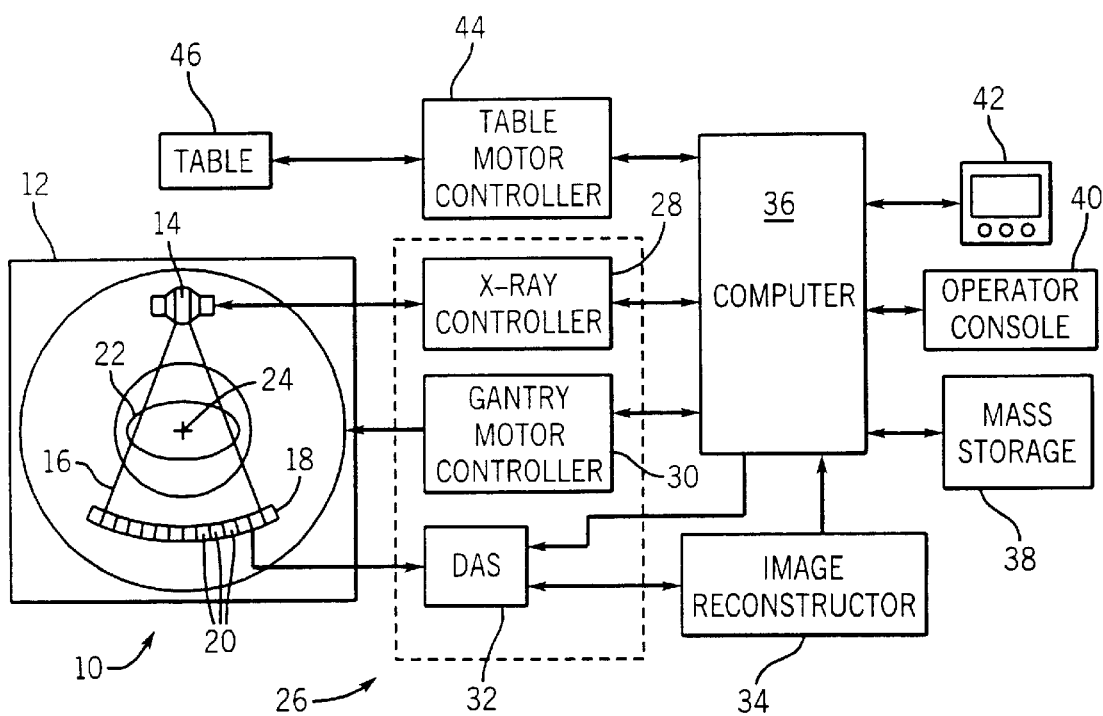
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 that together sense the projected x-rays that pass through an object 22, for example a medical patient. Each detector element 20 is relatively small, exemplary elements being on the order of 1.25 mm in effective length at isocenter in the z-axis 24. Each element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation or isocenter 24.

Rotation of gantry 12 and the operation of x-ray source 14 are governed by a control mechanism 26 of CT system 10.

Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20, converts the data to digital CT count signals may or may not store the CT counts in a mass storage device 38 for subsequent processing. Either during data acquisition or thereafter an image reconstructor 34 receives sampled and digitized x-ray data from DAS 32 or retrieves the data from storage device 38 and performs high-speed image reconstruction. The reconstructed image is provided to a computer 36 that stores the image in mass storage device 38 for subsequent examination.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 along a Z-axis 15 within gantry 12. Thus, table 46 moves portions of patient 22 through gantry opening 48 along axis 15.

Referring still to FIG. 2 detector elements 20 of array 18 are typically arranged in separate detector modules (not separately numbered in FIG. 2) that include a plurality of detector elements and then the modules are arranged side-by-side to form the arcuate shape illustrated in FIG. 2. An exemplary array includes 59 separate detector element arrays.

Figure 3:
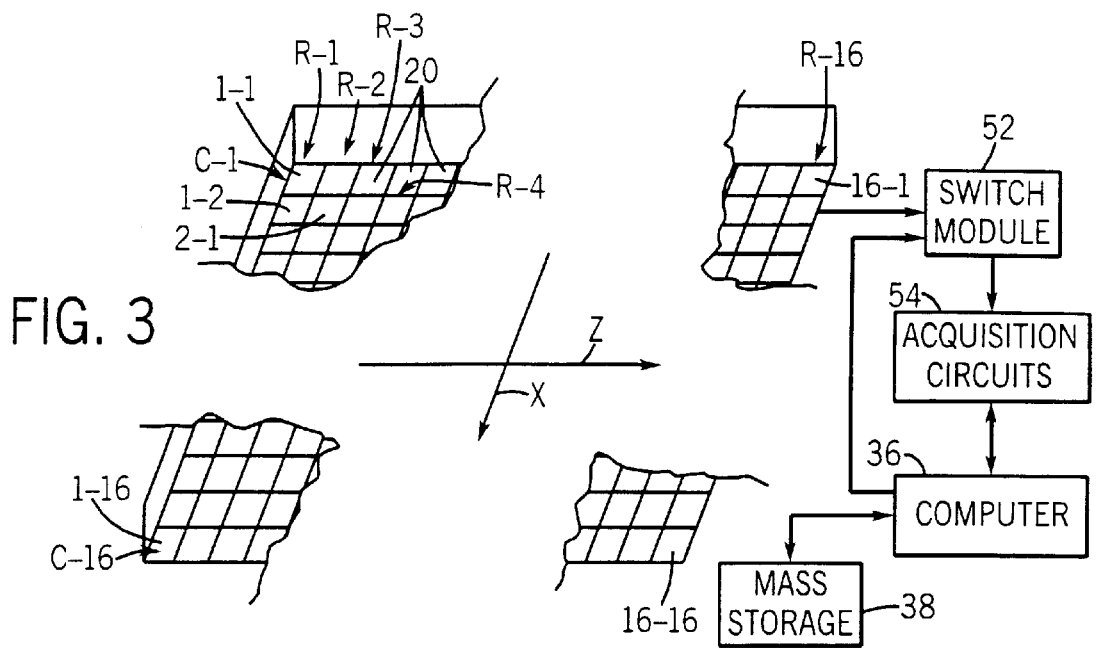
FIG. 3 is a schematic view of one of the CT modules of FIG. 2.

Referring to FIGS. 2 and 3, an exemplary module 50 is illustrated that includes 256 separate detectors 1-1 through 16-16 arranged in sixteen rows R-1 through R-16 and sixteen columns C-1 through C-16. In FIG. 3 rows R-1 through R-16 are aligned along an X-axis and columns C-1 through C-16 are aligned along a Z-axis. When modules are arranged in side-by-side fashion to form an arcuate array 18, the rows R-1 through R-16 in separate modules are aligned such that 16 separate and relatively long inter-module rows extending across the face of the array are formed. When mounted to gantry 12 array 18 is positioned such that the intermodule rows are perpendicular to the Z-axis 15. When so configured all of the data collected by each inter-module row during an acquisition corresponds to a single slice through the patient and can be used to form an image of a thin slice through the patient 22.

Referring still to FIGS. 2 and 3, DAS 32 includes, among other things, a switch module 52 and acquisition circuits or channels 54. Switch module 52 links elements 20 to acquisition channels 54 in a manner to be described in more detail below. Acquisition channel 54 receives intensity signals from linked elements 20 and convert the intensity signals to CT counts in a manner well known in the CT art. Channel 54 provide the CT counts to computer 36 which stores the CT counts in storage 38 for subsequent processing to generate a CT image.

Figure 4:
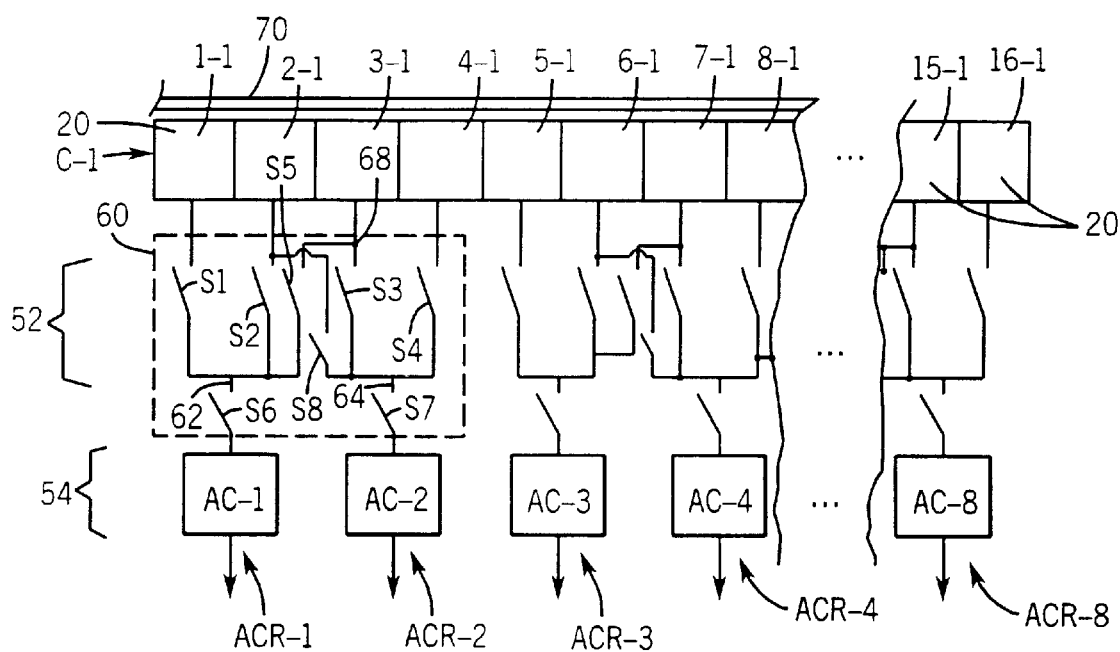
FIG. 4 is a schematic view illustrating several adjacent detector elements from separate rows within the module of FIG. 3.

Referring now to FIG. 4, a single column C-1 of elements 1-1 through 16-1 from FIG. 3 is illustrated along with corresponding switch module circuitry 52 and acquisition channel 54. As illustrated the exemplary system includes one acquisition channel 54 for every two detector elements in column C-1. For example, acquisition channels AC-1 and AC-2 are provided for acquiring intensity signals from detector elements 1-1, 2-1, 3-1 and 4-1, acquisition channels AC-3 and AC-4 are provided for acquiring intensity signals from detector elements 5-1, 6-1, 7-1 and 8-1 and so on.

For the purposes of this explanation the term "element sub-set" will be used to refer to four adjacent detector elements that are linked to the same two acquisition channels 54. For example, elements 1-1 through 4-1 are linked to acquisition channels AC-1 and AC-2 and therefore elements 1-1 through 4-1 constitute one element sub-set. Similarly elements 5-1 through 8-1 are linked to acquisition channels AC-3 and AC-4 and therefore those elements constitute a second element sub-set.

The switching circuit configurations linking element sub-sets to acquisition channels 54 are identical and therefore, in the interest of brevity, only the switching configuration 60 linking elements 1-1 through 4-1 to acquisition channels AC-1 through AC-2 will be described here in detail.

Configuration 60 includes first through eighth FET switches S1 through S8, respectively. Switch S1 links element 1-1 to a first common node 62 that is provided as an input to sixth switch S6. The output of sixth switch S6 is provided to acquisition channel AC-1. Second switch S2 links element 2-1 to common node 62 and hence to acquisition channel AC-1 through sixth switch S6. Third switch S3 links element 3-1 to a second common node 64 that is provided as an input to seventh switch S7. The output of seventh switch S7 is provided to acquisition channel AC-2. Fourth switch S4 links element 4-1 to common node 64 and hence to acquisition channel AC-2 through seventh switch S7. Fifth switch S5 links first common node 62 to the input of third switch S3. Similarly, eighth switch S8 links second common node 64 to the input of second switch S2.

Switches S1 through S8 can be opened and closed to select any sub-set of elements 1-1 through 4-1 for linkage to either of acquisition channels AC-1 or AC-2. For example, by closing only switches S1 and S6 only intensity signals from element 1-1 are provided to channel AC-1. By closing switches S1, S2 and S6 intensity signals from both elements 1-1 and 2-1 are provided to acquisition channel AC-1. By closing switches S1, S2, S3, S6 and S8 intensity signals from elements 1-1, 2-1 and 3-1 are provided to acquisition channel AC-1. By closing switches S1, S2, S3, S4, S6 and S8 intensity signals from each of elements 1-1 through 4-1 are provided to channel AC-1. Similar switch control can provide any combination of element outputs to acquisition channel AC-2.

Referring to FIGS. 2, 3 and 4, by controlling all switch channels corresponding to elements in inter-module rows in the same fashion data corresponding to various slices and slice thicknesses through a patient can be collected. For example, by collecting data from all elements aligned with row R-1 in FIG. 3, an image corresponding to a patient slice aligned with row R-1 can be generated. By combining data corresponding to rows R-1 and R-2 by closing switches S1, S2 and S6 and similarly configured switches linked to other elements in rows R-1 and R-2 an image corresponding to a relatively thicker patient slice aligned with rows R-1 and R-2 can be generated. By combining data corresponding to rows R-1 through R-4 by closing switches S1, S2, S3, S4, S6 and S8 and similarly configured switches linked to other elements in rows R-1 through R-4 an image corresponding to a relatively thicker patient slice aligned with rows R-1 through R-4 can be generated.

For the purposes of this explanation it will be assumed that acquisition channels 54 are arranged in acquisition channel (AC) rows adjacent detector rows so that there is one AC row for every inter-module detector row. Thus, in the present example where there are sixteen separate inter-module rows, there are 8 AC rows ACR-1 through ACR-8 (see FIG. 4 generally where one acquisition channel per each AC row is illustrated).

According to the present invention the opened and closed states of switches in module 52 are altered during data acquisition such that data corresponding to more slices through a patient than the number of AC rows ACR-1 through ACR-8 can be collected. To this end, referring again to FIG. 4, module 52 switches are controlled such that every AC row collects two separate data sets including a first data sub-set corresponding to a first inter-module row and a second data sub-set corresponding to a second inter-module row. The data sub-sets are collected during consecutive periods so that one data set is not corrupted by the other.

Referring still to FIGS. 3 and 4, during a first period switches S1 and S6 for each detector element 20 in row R-1 may be closed while associated switches S2 are opened such that AC row ACR-1 acquires a first data subset corresponding to row R-1. Then, during a second period following the first, switches S2 and S6 for each detector element 20 in row R-2 may be closed while associated switches SI are opened so that AC row ACR-1 acquires a second data sub-set corresponding to row R-2. This sequence of collecting first sub-set data followed by second sub-set data is repeated throughout the acquisition process during table translation and gantry rotation so that a helical data set is collected. After data acquisition the helical set is binned according to Z-axis "slices" through a patient and the binned data is then used to generate images.

In the alternative, where the table is translated through the gantry during gantry rotation and data acquisition, the switching between detector elements would continue during data acquisition to collect data corresponding to a large number of slices through the patient.

Referring still to FIGS. 3 and 4, in a fashion similar to that described above, switches S3, S4 and S7 and similar switches linking elements in rows R-3 an d R-4 to AC row ACR-2 can be controlled such that AC row ACR-2 collects first and second data sub-sets corresponding to rows R-3 and R-4. Other switches linking elements in each of rows R-4 through R-16 are also similarly controlled such that each AC row ACR-3 through ACR-8 collects first and second data sub-sets corresponding to two separate array rows so that a total of 16 separate data sub-sets, one sub-set for each of rows R-1 through R-16 are collected.

While it may seem that some intensity data would be lost during periods when an element is disconnected from an acquisition channel, it has been found that such losses can be minimized and reduced to acceptable levels by selecting relatively short acquisition periods. This is because current detector elements 20 have a memory characteristic.

To t his end, referring to FIG. 4, it is well known in the CT art that detector elements include, among other components, a scintillator crystal 70 that, upon absorbing an X-ray, generates light for a lumination period. The light is detected by one of the elements 20 (e.g., a photodiode) and turned into an electrical signal having an intensity related to the light intensity. During the lumination period, the crystal acts as a memory storing the X-ray for subsequent detection. In some cases the scintillator crystal has a primary speed sufficiently long that the scintillation operates as a single pole low pass IIR filter with a time constant that is approximately equal to or greater than the sampling frequency. If the scintillation response is too fast an integration circuit (not illustrated) positioned before the FETs, should be employed so that data is not lost.

By selecting the first and second periods to be shorter than the lumination period, beam signals absorbed by an element 20 during periods when the element is not linked to an acquisition channel 54 are detected during the next period. For instance, referring again to FIG. 4, assuming that element 1-1 is linked to channel AC-1 during a first period and that during the first period crystal 70 generates light adjacent element 2-1. During the first period channel AC-1 does not receive a signal from element 2-1 and therefore, during the first period no corresponding signal is generated. Exemplary periods will be approximately 0.5 ms to 1.5 ms and in some cases will be approximately 0.9 ms.

At the end of the first period element 2-1 is linked to acquisition channel AC-1 for the second period. During the second period, assuming the first period is shorter than the rumination period, element 2-1 detects the light generated by crystal 70 and provides an intensity signal to acquisition channel AC-1. Channel AC-1 then generates a CT count corresponding to the detected light and other light detected by element 2-1 during the second acquisition period.

Referring to FIGS. 3 and 4, computer 36 includes a processor (not illustrated) linked to the switch module 52 and channel 54 to control data acquisition by controlling the switch module switches. As data is provided by channels 54, the processor sorts the data and stores the data in mass storage 38 according to row, element and beam angle. After all data is collected during an acquisition period the processor generates one or more images using the stored data and can either store the images or provide the images for viewing via an interface (e.g., 42 in FIG. 2).

Figure 5:
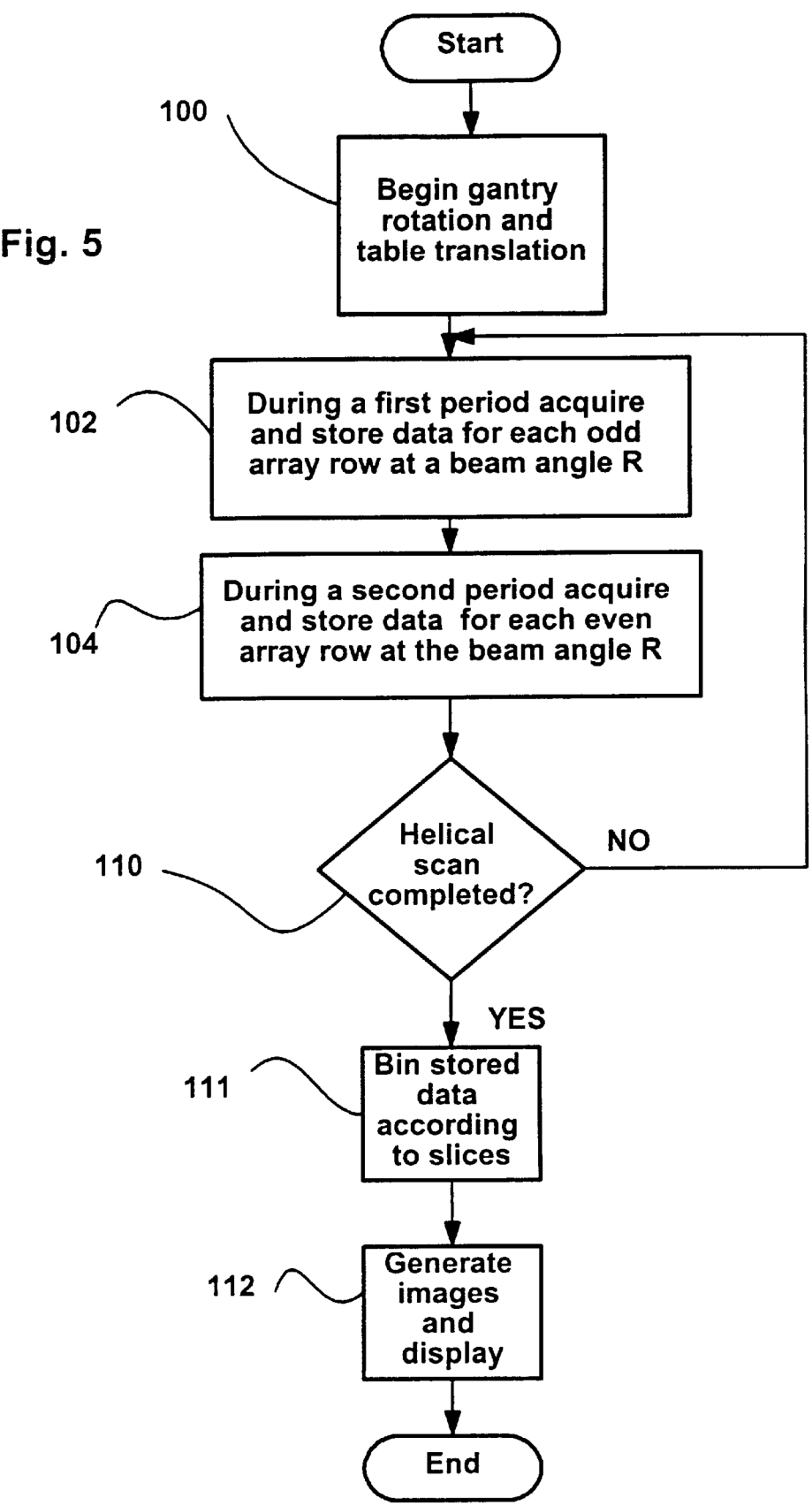
FIG. 5 is a flow chart illustrating one method according to the present invention.

Referring now to FIG. 5, a flow chart illustrating an exemplary method according to present invention is illustrated. Referring also to FIGS. 1–4, at process block 100 gantry rotation and table translation begin while the detector elements absorb radiation from source 14. At process block 102, during a first period, data is acquired for each odd array row at the specific beam angle R. Referring to FIG. 4, this means that each of the rows aligned with elements 1-1, 3-1, 5-1, 7-1, 9-1, 11-1, 13-1 and 15-1 is linked through a corresponding switch circuit in module 52 to one of the acquisition channels in acquisition channel rows ACR-1 through ARC-8. The acquired data is also stored at process block 102.

Next, at process block 104, during a second period the switches in module 52 are switched such that each even array row 2-1, 4-1, 6-1 through 16-1 is linked to an acquisition channel in one of acquisition channel rows ACR-1 through ACR-8. The outputs of rows ACR-1 through ACR-8 are provided to computer 36.

Next, at decision block 110 computer 36 determines whether or not the helical scan has been completed. If the scan has not been completed, control passes up to process block 102 and again steps through blocks 102, 104 and 110.

If, at decision block 110, the scan has been completed, data acquisition is complete and control passes to block 111 where computer 36 bins all the stored data according to slices so that, for separate slices through the patient, there is data from every angle about the patient. At block 112 computer 36 uses the slice data to generate images via a backprojection technique or some other suitable algorithm.

It should be understood that the methods and apparatuses described above are only exemplary and do not limit the scope of the invention, and that various modifications could be made by those skilled in the art that would fall under the scope of the invention. For example, referring again to FIG. 4, while simplified switching circuitry is illustrated for the purpose of simplifying this explanation, more complex circuitry would typically be employed enabling any of channels AC-1 through AC-4 to be linked to any of elements 1-1 through 8-1. Thus for instance, channels AC-1 through AC-4 could be linked to elements 1-1 through 4-1 during a first period and linked to elements 5-1 through 8-1 during a second period and so on. In addition, while the description above teaches a system where acquisition channels are alternately linked among two elements the invention contemplates a system where each channel may be alternately linked among more than two elements (e.g., 3, 4, 8, etc.).

To apprise the public of the scope of this invention, the following claims are made:

What is claimed is:

1. A method for use with a CT system including less acquisition channels than detector elements such that separate data-sets for each element cannot be acquired simultaneously via the acquisition channels, the method for acquiring data corresponding to a number of elements that is greater than the number of acquisition channels during an acquisition period and comprising the steps of:

for at least one acquisition channel, during each of N acquisition sub-periods, acquiring a data-set corresponding to a detector element where the detector elements for which data is acquired during each of the sub-periods are different elements; and storing the data-sets for subsequent use in constructing images.

2. The method of claim 1 wherein N is 2 and the step of acquiring includes acquiring first and second data subsets corresponding to first and second elements.

3. The method of claim 2 wherein the system includes a gantry for rotating the elements about an imaging area during a data acquisition period to obtain data from a plurality of different angles, the elements arranged in an array including rows and columns of elements such that the columns are aligned with an axis of gantry rotation and, wherein, the steps of acquiring first and second data sub-sets include the steps of acquiring the first and second data sub-sets corresponding to first and second rows of elements, respectively.

4. The method of claim 3 wherein the first and second rows are adjacent.

5. The method of claim 3 wherein the number of acquisition channels is half the number of detector rows and wherein the method is performed for each of the acquisition channels with a unique pair of first and second detector rows.

6. The method of claim 5 wherein each pair of detector rows comprises adjacent rows.

7. The method of claim 1 wherein the system includes a switching module that links elements to acquisition channels and wherein the steps of acquiring include causing the switching module to link elements to acquisition channels.

8. An apparatus for use with a CT system including less acquisition channels than detector elements such that separate data-sets for each element cannot be acquired simultaneously via the acquisition channels, the apparatus for acquiring data corresponding to a number of elements that is greater than the number of acquisition channels during an acquisition period, the apparatus comprising:

a processor running a pulse sequencing program to perform the steps of:

for at least one acquisition channel, during each of N acquisition sub-periods, acquiring a data-set corresponding to a detector element where the detector elements for which data is acquired during each of the sub-periods are different elements; and storing the data-sets for subsequent use in constructing images.

9. The apparatus of claim 8 wherein N is 2 and the step of acquiring includes acquiring first and second data subsets corresponding to first and second elements.

10. The apparatus of claim 9 wherein the system includes a gantry for rotating the elements about an imaging area during a data acquisition period to obtain data from a plurality of different angles, the elements arranged in an array including rows and columns of elements such that the columns are aligned with an axis of gantry rotation and, wherein, the processor runs the pulse sequencing program to perform the steps of acquiring first and second data sub-sets by performing the steps of acquiring the first and second data sub-sets corresponding to first and second rows of elements, respectively.

11. The apparatus of claim 10 wherein the processor runs the program to acquire data from first and second adjacent rows.

12. The apparatus of claim 9 wherein the number of acquisition channels is half the number of detector rows and wherein the processor runs the program to perform steps for each of the acquisition channels with a unique pair of first and second detector rows.

13. The apparatus of claim 12 wherein each pair of detector rows comprises adjacent rows.

14. The apparatus of claim 8 wherein the system includes a switching module that links elements to acquisition channels and wherein the processor runs the program to perform the steps of acquiring by causing the switching module to link elements to acquisition channels.

15. The apparatus of claim 8 further including a separate integrator between each element and each acquisition channel, each integrator integrating the signal generated by a linked element during the sub-periods when the element is not linked to the channel.

16. A method for use with a CT system including a detector array, a gantry and acquisition circuitry, the array including a plurality of detector elements arranged in element rows and columns and mounted to the gantry for rotation about a gantry rotation axis so that data can be collected from various beam angles wherein, the columns are aligned with the rotation axis, the acquisition circuitry arranged in acquisition channel rows including half as many acquisition channel rows as there are element rows, each acquisition channel row including a number of acquisition channels equal to the number of elements in an element row, uniquely associated with a pair of element rows and linkable to separate elements in each of the pair of associated element rows, the method for acquiring data corresponding to each element row during an acquisition period and comprising the steps of:

for each beam angle at which data is to be acquired:
for each acquisition row:
(a) during a first sub-period:
acquiring a first data-set corresponding to a first of the associated rows;
storing the first data-set;
(b) during a second sub-period:
acquiring a second data-set corresponding to a second of the associated rows;
storing the second data; and
repeating steps (a) and (b) until an acquisition period has lapsed.

17. The method of claim 16 wherein the first and second rows are adjacent.

18. The method of claim 16 wherein the system includes a switching module that links elements to acquisition channels and wherein the steps of acquiring include causing the switching module to link elements to acquisition channels.

\* \* \* \* \*